United States Patent [19]
Rogers et al.

[11] Patent Number: 6,124,278
[45] Date of Patent: Sep. 26, 2000

[54] ACYLBENZOXAZINES FOR ENHANCING SYNAPTIC RESPONSE

[75] Inventors: Gary A. Rogers, Santa Barbara, Calif.; Peter Johnstrom, Skondal, Sweden

[73] Assignee: The Regents of the University of California, Oakland, Calif.

[21] Appl. No.: 09/054,916

[22] Filed: Apr. 3, 1998

[51] Int. Cl.$^7$ ................ A61K 31/5365; A61K 31/55; C07D 498/04
[52] U.S. Cl. ................ 514/210.03; 514/212.06; 514/229.5; 514/230.5; 540/300; 540/301; 540/521; 544/89; 544/95
[58] Field of Search ............... 544/89, 95; 540/300, 540/301, 521; 514/210, 214, 229.5, 230.5, 210.03, 212.06

[56] References Cited

U.S. PATENT DOCUMENTS

| | | | |
|---|---|---|---|
| 5,426,192 | 6/1995 | Baumann et al. | 544/71 |
| 5,650,409 | 7/1997 | Rogers et al. | 514/230.2 |
| 5,736,543 | 4/1998 | Rogers et al. | 514/229.5 |
| 5,747,492 | 5/1998 | Lynch et al. | 514/249 |

FOREIGN PATENT DOCUMENTS

WO 94/02475   7/1993   WIPO.

*Primary Examiner*—Richard L. Raymond
*Attorney, Agent, or Firm*—Henry D. Coleman; R. Neil Sudol

[57] ABSTRACT

Compounds based on the benzoxazine ring system that are remarkably more potent than corresponding benzoyl piperidines for enhancing synaptic responses mediated by AMPA receptors are disclosed, as are methods for the preparation thereof, and methods for their use for treatment of subjects suffering from impaired nervous or intellectual functioning due to deficiencies in the number of excitatory synapses or in the number of AMPA receptors. The invention compounds can also be used for the treatment of non-impaired subjects for enhancing performance in sensory-motor and cognitive tasks which depend on brain networks utilizing AMPA receptors and for improving memory encoding.

23 Claims, No Drawings

ACYLBENZOXAZINES FOR ENHANCING SYNAPTIC RESPONSE

FIELD OF THE INVENTION

This invention relates to the prevention and treatment of cerebral insufficiency, including enhancement of receptor functioning in synapses in brain networks responsible for higher order behaviors. In a particular aspect, the invention relates to methods for the use of the compounds disclosed herein, and to methods for the preparation thereof.

BACKGROUND OF THE INVENTION

The release of glutamate at synapses at many sites in mammalian forebrain stimulates two classes of postsynaptic ionotropic receptors. These classes are usually referred to as AMPA/quisqualate and N-methyl-D-aspartic acid (NMDA) receptors. AMPA/quisqualate receptors mediate a voltage independent fast excitatory post-synaptic current (the fast epsc) whereas NMDA receptors generate a voltage-dependent, slow excitatory current. Studies carried out in slices of hippocampus or cortex indicate that the AMPA receptor-mediated fast epsc is by far the dominant component at most glutamatergic synapses under most circumstances.

AMPA receptors are not evenly distributed across the brain but instead are largely restricted to telencephalon and cerebellum. These receptors are found in high concentrations in the superficial layers of neocortex, in each of the major synaptic zones of hippocampus, and in the striatal complex, as reported by Monaghan et al., in *Brain Research* 324:160–164 (1984). Studies in animals and humans indicate that these structures organize complex perceptual-motor processes and provide the substrates for higher-order behaviors. Thus, AMPA receptors mediate transmission in those brain networks responsible for a host of cognitive activities.

For the reasons set forth above, drugs that enhance the functioning of AMPA receptors could have significant benefits for cognitive performance. Such drugs should also facilitate memory encoding. Experimental studies, such as those reported by Arai and Lynch, *Brain Research*, 598:173–184 (1992), indicate that increasing the size of AMPA receptor-mediated synaptic response(s) enhances the induction of long-term potentiation (LTP). LTP is a stable increase in the strength of synaptic contacts that follows repetitive physiological activity of a type known to occur in the brain during learning. Compounds that enhance the functioning of the AMPA form of glutamate receptors facilitate the induction of LTP and the acquisition of learned tasks as measured by a number of paradigms. Granger et al., *Synapse* 15:326–329 (1993); Staubli et al., *PNAS* 91:777–781 (1994); Arai et al., *Brain Res.* 638:343–346 (1994); Staubli et al., *PNAS* 91:11158–1162 (1994); Shors et al., *Neurosci. Let.* 186:153–156 (1995); Larson et al., *J. Neurosci.* 15:8023–8030 (1995); Granger et al., *Synapse* 22:332–337 (1996); Arai, et al., *JPET* 278:627–638 (1996); Lynch et al., *Internat. Clin. Psychopharm.* 11:13–19 (1996); Lynch et al., *Exp. Neurology* 145:89–92 (1997); Ingvar et al., *Exp. Neurology* 146:553–559 (1997); Hampson et al., *J. Neurosci.*, 18:2740–2747 (1998); Hampson, et al., *J. Neurosci.*, 18:2748–2763 (1998) and International Patent Application Publication No. WO 94/02475 (PCT/US93/06916) (Lynch and Rogers, Regents of the University of California).

There is a considerable body of evidence showing that LTP is the substrate of memory. For example, compounds that block LTP interfere with memory formation in animals, and certain drugs that disrupt learning in humans antagonize the stabilization of LTP, as reported by del Cerro and Lynch, *Neuroscience* 49:1–6 (1992). A possible prototype for a compound that selectively facilitates the AMPA receptor was disclosed by Ito et al., *J. Physiol.* 424:533–543 (1990). These authors found that the nootropic drug aniracetam (N-anisoyl-2-pyrrolidinone) increases currents mediated by brain AMPA receptors expressed in Xenopus oocytes without affecting responses by γ-aminobutyric acid (GABA), kainic acid (KA), or NMDA receptors. Infusion of aniracetam into slices of hippocampus was also shown to substantially increase the size of fast synaptic potentials without altering resting membrane properties. It has since been confirmed that aniracetam enhances synaptic responses at several sites in hippocampus, and that it has no effect on NMDA-receptor mediated potentials. See, for example, Staubli et al., in *Psychobiology* 18:377–381 (1990) and Xiao et al., *Hippocampus* 1:373–380 (1991). Aniracetam has also been found to have an extremely rapid onset and washout, and can be applied repeatedly with no apparent lasting effects; these are valuable traits for behaviorally-relevant drugs. Unfortunately, the peripheral administration of aniracetam is not likely to influence brain receptors. The drug works only at high concentrations (~1.0 mM) and Guenzi and Zanetti, *J. Chromatogr.* 530:397–406 (1990) report that about 80% of the drug is hydrolyzed to anisoyl-GABA following peripheral administration in humans. The metabolite, anisoyl-GABA, has been found to have only weak aniracetam-like effects.

A class of compounds that do not display the low potency and inherent hydrolytic instability characteristic of aniracetam has recently been disclosed. These compounds, termed "Ampakines", are disclosed in International Patent Application Publication No. WO 94/02475 (PCT/US93/06916) (Lynch and Rogers, Regents of the University of California). The Ampakines generally are substituted benzamides, are chemically more stable than aniracetam, and show improved bioavailability as judged by experiments performed by Positron Emission Tomography (PET) [see, for example, Staubli et al., in *PNAS* 91:11158–11162 (1994)]. Additional Ampakines in the form of benzoyl piperidines and pyrrolidines have also been discovered and are the subject of pending U.S. Pat. No. 5,650,450. A new class of Ampakines, benzoxazines, have been discovered recently to have unexpectedly high activity in in vitro and in vivo models for assessing the probability of producing cognition enhancement [Rogers and Lynch "Benzoxazines for Enhancing Synaptic Response", U.S. Pat. No. 5,736,543, issued Apr. 7, 1998. Further structure-activity development has uncovered a new series of compounds, acyl benzoxazines, that produce potent responses in in vitro assays of AMPA receptor activation and show significantly improved biostability compared to isomeric benzoxazines. These compounds are disclosed herein.

SUMMARY OF THE INVENTION

It has now been discovered that synaptic responses mediated by AMPA receptors are increased by administration of a novel class of acyl benzoxazine derivatives. The ability of the novel compounds of this invention to increase AMPA receptor-mediated responses makes the compounds useful in serving a variety of purposes, including facilitating the learning of behaviors dependent upon AMPA receptors, and as therapeutic drugs in conditions in which AMPA receptors or synapses utilizing these receptors are reduced in numbers or efficiency, or in those circumstances when enhanced excitatory synaptic activity would be beneficial. It has been unexpectedly discovered that the compounds of the present invention evidence enhanced bioavailability and increased metabolic stability compared to compounds of the prior art. In addition, the compounds of the present invention, which were originally thought to be completely inactive or to evidence significantly reduced activity compared to the prior art compounds, unexpectedly exhibited enhanced activity compared to the prior art compounds.

Invention compounds are demonstrated in the examples that follow to possess surprising biological activity as evidenced by their ability to increase AMPA receptor function in slices of rat hippocampus, to be substantially more metabolically stable than structurally related Ampakines, and to promote improvement in relevant memory tasks, such as performance in an eight-arm radial maze. These and other aspects and advantages of the invention will become apparent from the description that follows.

DETAILED DESCRIPTION OF THE INVENTION AND PREFERRED EMBODIMENTS

The compounds of the present invention are acylbenzoxazines having the following formula:

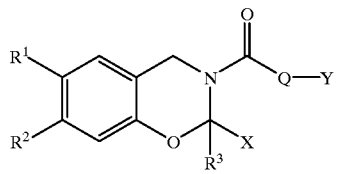

Wherein:

$R^1$ and $R^2$ are either individual monovalent moieties or joined together to form a single divalent moiety. As monovalent moieties, $R^1$ and $R^2$ are either the same or different and are each either H, —$CH_2OR^4$, or —$OR^4$ provided that at least one of $R^1$ and $R^2$ is not H, and in which $R^4$ is either H, $C_1$–$C_6$ alkyl, $C_1$–$C_6$ fluoroalkyl, $C_7$–$C_{12}$ arylalkyl, or $C_3$–$C_{10}$ heteroarylalkyl. As a single divalent moiety, $R^1$ and $R^2$ together form a group selected from

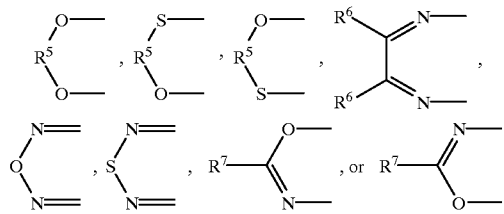

wherein:

$R^5$ is —$(CR_2)_m$—, —$CR_2CR_2$—, or —$CR=CR$—, R is H, halogen, cyano, $C_1$–$C_6$ alkyl, $C_1$–$C_6$ haloalkyl, $C_7$–$C_{12}$ arylalkyl, or $C_3$–$C_{10}$ heteroarylalkyl and is either the same or different in any $R^5$;

$R^6$ is H, cyano, —OH, $C_1$–$C_6$ alkyl, $C_1$–$C_6$ fluoroalkyl, $C_7$–$C_{12}$ arylalkyl, or $C_3$–$C_{10}$ heteroarylalkyl, $C_3$–$C_{10}$ heteroarylalkyl, or —$OR^4$, and $R^4$ is the same as above;

$R^7$ is H, $C_1$–$C_6$ alkyl, $C_1$–$C_6$ fluoroalkyl, $C_7$–$C_{12}$ arylalkyl, or $C_3$–$C_{10}$ heteroarylalkyl;

$R^3$ is H, $C_1$–$C_6$ alkyl, or $C_1$–$C_6$ fluoroalkyl;

Q is a substituted or unsubstituted lower alkylene, cycloalkyl, aryl, arylalkyl, or heteroarylalkyl;

X and Y are both independently H, or together form a covalent bond or —$(CH_2)_n$—linking Q to the benzoxazine ring;

m is 1 or 2; and n is 1 or 2.

The term "alkyl" is used herein to include both straight-chain, branched-chain, and cycloalkyl species. The term "fluoroalkyl" is used herein to include both single and multiple fluorine substitutions, with perfluorinated $C_1$–$C_3$ moieties being preferred. The term "aryl" includes both substituted and unsubstituted carbocylic and heterocylic aromatic species, such as phenyl, tolyl, pyridyl, imidazoyl, alkylenedioxyphenyl, etc.

Thus, for those compounds in which $R^1$ and $R^2$ are individual monovalent moieties, preferred compounds are those in which one of these two moieties is H and the other is —$OR^4$ where $R^4$ is either $C_1$–$C_6$ alkyl or $C_1$–$C_3$ fluoroalkyl, with $R^4$ more preferably being either $C_1$–$C_3$ alkyl or $C_1$–$C_2$ fluoroalkyl, still more preferably —$CH(CH_3)_2$ or —$CF_3$, and most preferably —$CH(CH_3)_2$. $R^3$ is preferred to be H, and Q is preferred to be lower alkylene, and X and Y together form a covalent bond.

The term "effective amount" or "therapeutically effective amount" is used throughout the present application to describe an amount or concentration of one or more of the compounds according to the present invention which is used to produce a desired effect or treat a specific condition in a patient or subject. Compounds according to the present invention may be used to improve the performance of a patient on sensory-motor problems, to enhance the performance of subjects involving cognitive tasks dependent upon brain networks utilizing AMPA receptors, to improve the strength of memory encoding or to improve brain functioning in subjects with deficiencies in the number of excitatory synapses or AMPA receptors. The present compounds may also be used in effective amounts to decrease the time needed for a subject to learn a cognitive, motor or perceptual task, or for decreasing the quantity and/or severity of errors made by a subject in recalling a cognitive, motor or perceptual task. The present compounds are also useful for treating human subjects to enhance synaptic response mediated by AMPA receptors. In addition, the present compounds may be used to treat schizophrenia, schizophreniform behavior or depression in a human patient or subject. In each instance where the present compounds are used, they are used in amounts or concentrations effective for producing a desired effect or for treating a specific condition in a patient.

The term "patient" or "subject" is used throughout the specification to describe an animal, including a human, to whom treatment or use with the compounds or compositions according to the present invention is provided. For treatment or use with/or of those conditions or disease states which are specific for a specific animal (especially, for example, a human subject or patient), the term patient or subject refers to that particular animal.

The compounds of the present invention can be synthesized in a variety of ways, using conventional synthetic chemistry techniques. One method for the preparation of the compounds of the present invention comprises:

preparing an ortho hydroxy substituted benzyl amine by contacting a suitably substituted phenol with hydroxymethylphthalimide in an inert solvent with a suitable catalyst such as an aryl or alkylsulfonic acid or other Lewis acid catalyst known to those skilled in the art. After the benzylic amine is liberated by treatment with hydrazine in ethanol, it is acylated by a suitably activated carboxylic acid to produce an amide. Ring closure to an acylbenzoxazine can be achieved by treatment with formaldehyde, or a suitably substituted higher aldehyde to give structures of the type shown below:

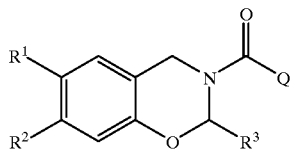

wherein each $R^1$ and $R^2$ is as defined above and in addition may be an aromatic carbocyclic, aromatic heterocyclic, or benzyl group, any of which may have structurally diverse variable substituents.

Another method for the preparation of the compounds of the present invention comprises contacting the benzyl amine with an activated acid that contains an incipient aldehyde or ketone in the form of an acetal or ketal or oxidizable alcohol. The aldehyde or ketone is generated and catalyzed by a strong acid in a solvent of low basicity to cyclyze with the amide nitrogen and the phenol to give rotationally restricted structures of the type shown below:

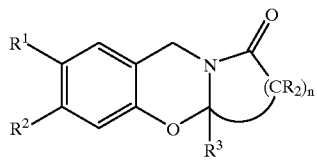

wherein each $R^1$ and $R^2$ is as defined above and in addition may be an aromatic carbocyclic, aromatic heterocyclic, or benzyl group, any of which may have structurally diverse variable substituents.

This application is related to U.S. Pat. No. 5,736,543, issued Apr. 7, 1998 and to patent application Ser. No. PCT/US93/06916, filed Jul. 23, 1993, published as WO 94/02475 on Feb. 3, 1994, and filed as U.S. patent application Ser. No. 08/374,584 on Jan. 24, 1995, now U.S. Pat. No. 5,747,492, the relevant teachings of which are incorporated herein by reference.

Having generally described the invention, reference is now made to the following examples which are intended to illustrate certain of the preferred embodiments and comparisons. The included examples are not to be construed as limiting the scope of this invention as is more broadly set forth above and in the appended claims.

EXAMPLE 1

5a,6,7,8-Tetrahydro-1,3-dioxolo[4,5-g]pyrrolo[2,1-b][1,3]benzoxazine-8(10H)-one p-Toluenesulfonic acid monohydrate (3.61 g, 19.0 mmol) was dried by azeotropic distillation in a chloroform solution (100 mL). The remaining solution (50 mL) was cooled, 9.14 g (66.2 mmol) sesamol, 10.01 g (57 mmol) N—(hydroxymethyl)-phthalimide, and 100 mL chloroform were added, and the resulting green solution was refluxed overnight. The black reaction mixture was cooled to ambient, diluted to 500 mL with chloroform, and washed three times with saturated sodium bicarbonate. The pooled aqueous phases were back extracted with ethyl acetate, which was combined with the chloroform solution and dried over sodium sulfate. The residue that resulted from evaporation of solvents on a rotary evaporator was taken up in dichloromethane and filtered through a short column of silica gel. A dichloromethane rinse of the silica gel was combined with the eluent and evaporated to yield 9.3 g of N—(2-hydroxy-4,5-methylenedioxybenzyl)-phthalimide as a yellow solid (55%), which exhibited one spot on TLC ($R_f$=0.6; dichloro-methane). IR: 1768 and 1699 cm$^{-1}$. $^1$HNMR (200 MHz): δ 7.81–7.90 (2H, m); 7.70–7.79 (2H, m); 7.76 (1H, s); 6.86 (1H, s); 6.52 (1H, s); 5.88 (2H, s); and 4.73 ppm (2H, s).

N-(2-Hydroxy-4,5-methylenedioxybenzyl)phthalimide (2.0 g; 6.7 mmol) was dissolved in 20 mL tetrahydrofuran (THF) under argon. Sodium hydride (0.27 g; 6.78 mmol) as a 60% dispersion in mineral oil was added portion-wise to the stirred solution and after 30 min, 0.65 mL (7.01 mmol) chloromethyl ethyl ether was added. The mixture was allowed to stand overnight, following which additional equivalents of sodium hydride and chloromethyl ethyl ether were added and allowed to react for an additional four hr. The volume of solution was reduced on a rotary evaporator and the residue was partitioned between water and dichloromethane. The aqueous phase was further extracted with dichloromethane (three times) and the pooled organic layers were combined and washed with 10% sodium hydroxide (three times) and with a saturated brine solution before being dried over sodium sulfate. Evaporation of the solvent and dissolution of the resulting brown liquid in ethyl ether gave crystals, which were collected by filtration and washed with ethyl ether/petroleum ether (1:1). The supernatant and wash solutions were pooled and additional product was isolated by silica gel chromatography (10%–20% ethyl acetate/hexane) for a total yield of 1.70 g of N-(2-ethoxymethoxy-4,5-methylene-dioxybenzyl)phthalimide (71%). IR (thin film): 1770 and 1709 cm$^{-1}$. $^1$HNMR (200 MHz): δ 7.80–7.90 (2H, m); 7.67–7.77 (2H, m); 6.77 (2H, s); 5.88 (2H, s); 5.19 (2H, s); 4.86 (2H, s); 3.73 (2H, q, J=7.04 Hz); and 1.21 ppm (3H, t, J=7.15 Hz).

N-(2-Ethoxymethoxy-4,5-methylenedioxybenzyl) phthalimide (1.70 g, 4.77 mmol) was treated with 0.5 mL (16 mmol) hydrazine in 90 mL refluxing ethanol for three hr. The reaction mixture was cooled and the phthalhydrazide was removed by filtration and washed three times with ethyl ether. The organic solutions were combined and evaporated to dryness on a rotary evaporator to yield a residue, which was taken up in dichloromethane. The organic solution was washed three times with 10% sodium hydroxide and the combined aqueous solutions were back-extracted with dichloromethane two times. The combined organic solutions were washed with brine and dried over sodium sulfate/potassium carbonate. Evaporation of the solvent gave of 2-ethoxymethoxy-4,5-methylenedioxybenzylamine as a slightly yellow liquid (0.98 g, 92% yield) that solidified upon standing. IR: 3298 cm$^{-1}$. $^1$HNMR (200 MHz): δ 6.77 (1H, s); 6.75 (1H, s); 5.91 (2H, s); 5.18 (2H, s); 3.74 (2H, q, J=7.1 Hz); 3.73 (2H, s); 1.45 (2H, br s); and 1.24 ppm 3H, t,J=7.1 Hz).

4,4-Diethoxybutyric acid (716 mg, 4.06 mmol) was activated by addition to a solution of 613 mg (3.78 mmol) of carbonyl diimidazole in 10 mL dichloromethane. The solution was stirred for two hr, after which a solution of 978 mg (4.35 mmol) of 2-ethoxymethoxy-4,5-methylenedioxybenzylamine in 15 mL dichloromethane was added and allowed to stand for three days. The solution was washed with phosphate buffer (0.1 M, pH 6.8) three times and once with brine before being dried over sodium sulfate. Evaporation of the solvent gave 1.42 g (98% yield) of yellow liquid. IR: 1644 cm$^{-1}$. $^1$HNMR (200 MHz): δ 6.78

(1H, s); 6.75 (1H, s); 5.95–6.08 (1H, br t); 5.91 (2H, s); 5.17 (2H, s); 4.49 (1H, t, J=5.5 Hz); 4.34 (2H, d, J=5.8 Hz); 3.78–3.89 (6H, m); 2.26 (2H, t, J=5.8 Hz); 1.94 (2H, dt, J=7.5 & 5.4 Hz); and 1.13–1.30 ppm (9H, t, J=7.0 Hz).

The amide/acetal (1.20 g, 3.12 mmol) from above was combined with 4 mL 2-propanol and 200 µL conc. HCl in 20 mL THF and allowed to stand at room temperature overnight. The residue resulting from evaporation of the solvents was partitioned between water and dichloromethane. The aqueous layer was extracted with dichloromethane three times and the pooled organic fractions were washed twice with 10% HCl, three times with 10% sodium hydroxide, and once with brine prior to being dried over sodium sulfate. Removal of the solvent gave an off-white solid that was purified on silica gel (20% ethyl acetate/hexane) and crystallized from dichloromethane/ethyl ether to yield 301 mg (41%) of the acylbenzoxazine with m.p.=163–164° C. IR: 1697 cm$^{-1}$. $^1$HNMR (200 MHz): δ 6.51 (1H, s); 6.40 (1H, s); 5.91 (2H, s); 5.31 (1H, dd, J=5.3 & 1.6 Hz); 4.85 (1H, d, J=16.5Hz); 4.20 (1H, d, J=16.4 Hz); and 2.14–2.69 ppm (4H, m).

EXAMPLE 2

6a,7,8,9-Tetrahydro-1,4-dioxin[2,3-g]pyrrolo[2,1-b] [1,3]benzoxazine-9(11H)-one

N-(hydroxymethyl)phthalimide (97.46 g, 42.1 mmol), 3,4-ethylenedioxyphenol (96.4 g, 42.1 mmol), and p-toluenesulfonic acid monohydrate (0.87 g, 4.6 mmol) were dissolved in 80 mL chloroform and the mixture was refluxed for three days under a Dean-Stark trap with occasional removal of water. The brown solution was filtered through a silica plug, the silica plug was washed with chloroform, and the combined organic solutions were evaporated to yield a yellow solid that was purified by flash chromatography with dichloromethane as eluent. The intermediate was obtained as a yellow solid (5.8 g) composed of a mixture of isomers, which was used without further purification.

The solid from above (1.4 g, 4.5 mmol) was dissolved in 15 mL THF and treated with 0.7 g (7.4 mmol) chloromethyl ethyl ether and 0.3 g (7.5 mmol) sodium hydride (as a 60% dispersion in mineral oil) under argon for one hr. Water was added and the separated aqueous phase was extracted three times with dichloromethane. The combined organic phases were washed three times with 10% sodium hydroxide and once with brine prior to being dried over sodium sulfate. Evaporation of the solvent gave an oil that dissolved in ethyl ether and crystallized to yield 0.63 g (38%) white crystals. M.p.=97–98.5° C. IR: 1771 and 1709 cm$^{-1}$. $^1$HNMR (200 MHz): δ 7.6–7.9 (4H, m); 6.70 (1H, s); 6.69 (1H, s); 5.17 (2H, s); 4.82 (2H, s); 4.18 (4H, m); 3.71 (2H, q, J=7.2 Hz); and 1.2 ppm (3H, t, J=7.1 Hz).

N-(2-ethoxymethoxy-4,5-ethylenedioxybenzyl) phthalimide (625 mg, 1.69 mmol) was mixed with 0.2 mL (6.4 mmol) hydrazine in 30 mL ethanol and refluxed for three hr. The reaction mixture was cooled, 30 mL ethyl ether was added to the mixture, and a white precipitate was removed by filtration. The filter cake was washed three times with diethyl ether and the combined organic solutions were evaporated to yield a residue that was partitioned between ethyl ether and 10% sodium hydroxide. The organic phase was washed three times with 10% sodium hydroxide, and the aqueous washes were combined and back-extracted twice with dichloromethane. The organic solutions were combined and washed with brine and dried over sodium sulfate/potassium carbonate. Subsequent evaporation of solvent gave 2-ethoxymethoxy-4,5-ethylenedioxybenzylamine as a light yellow oil (346 g, 86% crude), which solidified upon standing. IR: 3375 cm$^{-1}$.

4,4-Diethoxybutyric acid (270 mg, 1.53 mmol) was activated by addition to a solution of 213 mg (1.31 mmol) of carbonyl diimidazole in 5 mL dichloromethane. The solution was stirred for 30 min, after which a solution of 347 mg (1.45 mmol) of 2-ethoxymethoxy-4,5-ethylenedioxybenzylamine in 1 mL dichloromethane was added and allowed to stand over night. The solution was washed with phosphate buffer (0.1 M, pH 6.8) three times and once with brine before being dried over sodium sulfate. The solution was filtered through a small plug of silica gel and evaporated to yield 436 mg (84% crude) of an oil. IR: 3293 and 1644 cm$^{-1}$.

The amide/acetal (436 mg, 1.1 mmol) from above was combined with 2 mL 2-propanol and 100 µL conc. HCl in 10 mL THF and allowed to stand at room temperature overnight. The residue resulting from evaporation of the solvents was taken up in dichloromethane and washed three times with 10% HCl, three times with 10% sodium hydroxide, and once with brine prior to being dried over sodium sulfate. Removal of the solvent gave a white solid that was crystallized from dichloromethane/ethyl ether and washed twice with ethyl ether/petroleum ether to yield 123 mg (45%) of the acylbenzoxazine with m.p.=151–152° C. IR: 1708 and 1689 (sh) cm$^{-1}$. $^1$HNMR (200 MHz): δ 6.58 (1H, s); 6.41 (1H, s); 5.32 (1H, dd); 4.86 (1H, d, J=16.7 Hz); 4.22 (4H, m);4.20 (1H, d, J=16.3 Hz); and 2.12–2.70 ppm (4H, m).

EXAMPLE 3

6a,7,8,9-Tetrahydro- 1,4-dioxan[2,3-g]pyrido[2,1-b] [1,3]benzoxazine-10(10H,12H)-dione Trimethylaluminum as a 2 M solution in toluene (2.3 mL, 4.6 mmol ) was added to a two-neck flask under argon and cooled to −5 to −10° C. 2-Ethoxymethoxy-4,5-ethylenedioxybenzylamine (1.0 g, 4.18 mmol; as a mixture of isomers) in 5 mL dry chloroform was added to the flask and the resulting solution was held at the same temperature for 20 min. After the solution was allowed to warm to ambient temperature, 0.81 g (4.6 mmol) of methyl 5,5-dimethoxyvalerate was added and the resulting solution was refluxed over night. The reaction was quenched with methanol and phosphate buffer (0.1 M, pH 6.8) and extracted three times with dichloromethane. The pooled organic phases were washed with phosphate buffer three times, once with brine, and dried over sodium sulfate. The amide was purified to a light yellow oil on silica gel with dichloromethane/ethyl ether (4:1) as eluent and proved (via NMR) to be a mixture of free and protected phenolic compounds that was used without further purification. IR: 3279 and 1632 )cm$^{-1}$.

The oil from above was dissolved in 10 mL THF, 2 mL 2-propanol, and 100 µL conc. HCl and allowed to stand for 24 hr. The solvent was removed under vacuum and the residue was taken up in dichloromethane, which was washed three times with 10% HCl, three times with 10% sodium hydroxide, and once with brine before being dried over sodium sulfate. Evaporation of the solvent gave a white solid that was crystallized from dichloromethane/ethyl ether to yield 141 mg of the ε-lactam. As crystals of the product are heated, a transformation occurs at 147° C. to give a new form that melts at 163° C. IR: 1647 and 1639 cm$^{-1}$ (unresolved doublet). $^1$HNMR (200 MHz): δ 6.58 (1H, s); 6.39 (1H, s); 5.31 (1H, d, J=16.4 Hz); 5.16 (1H, t, J=3.4 Hz);

4.22 (4H, m); 4.12 (1H, d, J=16.7 Hz); 2.30–2.60 (2H, m); 1.00–2.20 (3H, m); and 1.70–1.90 ppm (1H, m).

EXAMPLE 4

5a,6,7,8-Tetrahydro-1,3-dioxolo[4,5-g]pyrrolo[2,1-b][1,3]benzoxazine-8,10(10H)-dione 4,5-Methylenedioxysalicylamide (496 mg; 2.74 mmol) was dissolved in 10 mL trifluoroacetic acid to which was added 491 mg (2.79 mmol) 4,4-diethoxybutyric acid. After 24 hr the reaction solution was reduced to 5 mL on a rotary evaporator and addition of an additional 526 mg of 4,4-diethoxybutyric acid caused a white precipitate to form. The trifluoroacetic acid was removed by evaporation and the solid was taken up in turn by ethyl acetate and ethanol and again isolated by evaporation of the solvent. Finally, the solid was subjected to high vacuum. IR: 1720, 1657, 1617, 1470, 1260, and 1177 cm$^{-1}$. $^1$HNMR (200 MHz; $d_6$DMSO/CDCl$_3$): δ 8.32 (1H, br s); 7.17 (1H, s); 6.47 (1H, s); 6.02 (2H, s); 5.25 (1H, t, J=4.5 Hz); 2.48–2.6 (2H, m); and 2.06–2.2 ppm (2H, m).

The intermediate acid was added to a solution of 1.09 g (6.17 mmol) of carbonyl diimidazole in 20 mL of methylene dichloride. After 24 hr a white milky suspension was observed. A TLC analysis suggested some starting material remained and therefore an additional 474 mg CDI was added to the suspension. No further reaction was observed and the white solid was isolated by filtration and washed with dichloromethane. UV and IR spectra indicate that this intermediate (310 mg) is the acyl imidazole and therefore it was suspended in 10 mL dichloromethane and treated with 105 mg triethylamine for 4 days, at which time the reaction solution was homogeneous. The solution was washed with 10% HCl (3 times) and once with brine, and finally dried over Na$_2$SO$_4$. Removal of the solvent by evaporation yielded 205.6 mg white solid. The solid was dissolved in trifluoroacetic acid, but no change occurred (via TLC) over a period of days. The product was re-isolated and crystallized from CHCl$_3$/Et$_2$O to yield material with m.p.=224–225° C. IR: 1750 (s), 1673 (m), and 1625 (m) cm$^{-1}$. $^1$HNMR (500 MHz) δ 7.4 (1H, s); 6.47 (1H, s); 6.05 (2H, s); 5.77 (1H, dd, J=5.0 & 7.1 Hz); 2.69–2.78 (1H, m); 2.53–2.64 (2H, m); and 2.29–2.39 ppm (1H, m). FAB MS: m/z=248 (P+1).

The above-described compounds can be incorporated into a variety of formulations (e.g., capsule, tablet, timed-release capsule, syrup, suppository, injectable form, transdermal patch, etc.) for administration to a subject. Similarly, various modes of delivery (e.g., oral, bucal, rectal, parenteral, intraperitoneal, cutaneous, etc.) can be employed. Dose levels employed can vary widely, and can readily be determined by those of ordinary skill in the art. Typically, amounts in the milligram up to decigram quantities are employed. Oral administration (one to four times daily) is clearly preferred. Because of the unexpectedly favorable bioavailability and stability of compounds according to the present invention may be given orally as few as twice or even once, daily. Subjects contemplated for treatment with the invention compounds include humans, domesticated animals, laboratory animals, and the like.

Invention compounds can be used, for example, as a research tool for studying the biophysical and biochemical properties of the AMPA receptor and the consequences of selectively enhancing excitatory transmission on the operation of neuronal circuitry. Because invention compounds reach central synapses, they will allow for testing of the behavioral effects of enhancing AMPA receptor currents.

Metabolically stable compounds which are positive modulators of AMPA currents have many potential applications in humans. For example, increasing the strength of excitatory synapses could compensate for losses of synapses or receptors associated with aging and brain disease (e.g., Alzheimer's). Enhancing AMPA receptors could cause more rapid processing by multisynaptic circuitries found in higher brain regions and thus could produce an increase in perceptual-motor and cognitive performance. As another example, because increasing AMPA receptor-mediated responses facilitates synaptic changes of the type believed to encode memory, metabolically stable AMPA modulators are expected to be functional as memory enhancers.

Additional applications contemplated for the compounds of the present invention include improving the performance of subjects with sensory-motor problems dependent upon brain networks utilizing AMPA receptors; improving the performance of subjects impaired in cognitive tasks dependent upon brain networks utilizing AMPA receptors; improving the performance of subjects with memory deficiencies; and the like, as previously described.

Further contemplated uses for the compounds of the present invention include correcting suboptimal system level communication between and among brain regions responsible for behaviors associated with psychiatric disorders, such as schizophrenia.

Accordingly, invention compounds, in suitable formulations, can be employed for decreasing the amount of time needed to learn a cognitive, motor or perceptual task. Alternatively, invention compounds, in suitable formulations, can be employed for increasing the time for which cognitive, motor or perceptual tasks are retained. As another alternative, invention compounds, in suitable formulations, can be employed for decreasing the quantity and/or severity of errors made in recalling a cognitive, motor or perceptual task. Such treatment may prove especially advantageous in individuals who have suffered injury to the nervous system, or who have endured disease of the nervous system, especially injury or disease which affects the number of AMPA receptors in the nervous system. Invention compounds are administered to the affected individual, and thereafter, the individual is presented with a cognitive, motor or perceptual task.

The invention will now be described in greater detail by reference to the following non-limiting examples.

EXAMPLE 5

In Vitro Physiological Testing

The physiological effects of invention compounds can be tested in vitro with slices of rat hippocampus according to the following procedure. Excitatory responses (field EPSPs) are measured in hippocampal slices, which are maintained in a recording chamber continuously perfused with artificial cerebrospinal fluid (ACSF). During a 15–30 minute interval, the perfusion medium is switched to one containing various concentrations of the test compounds. Responses collected immediately before and at the end of drug perfusion were superimposed in order to calculate both the percent increase in EPSP amplitude and percent increase in the width of the response at one-half the peak height (half-width).

To conduct these tests, the hippocampus was removed from anesthetized, 2 month old Sprague-Dawley rats and in vitro slices (400 micrometers thick) were prepared and maintained in an interface chamber at 35° C. using conventional techniques [see, for example, Dunwiddie and Lynch,

*J. Physiol.* 276: 353–367 (1978)]. The chamber was constantly perfused at 0.5 mL/min with ACSF containing (in mM): NaCl 124, KCl 3, $KH_2PO_4$ 1.25, $MgSO_4$ 2.5, $CaCl_2$ 3.4, $NaHCO_3$ 26, glucose 10 and L-ascorbate 2. A bipolar nichrome stimulating electrode was positioned in the dendritic layer (stratum radiatum) of the hippocampal subfield CA1 close to the border of subfield CA3.

Current pulses (0.1 msec) through the stimulating electrode activate a population of the Schaffer-commissural (SC) fibers that arise from neurons in the subdivision CA3 and terminate in synapses on the dendrites of CA1 neurons. Activation of these synapses causes them to release the transmitter glutamate. Glutamate binds to the post-synaptic AMPA receptors which then transiently open an associated ion channel and permit a sodium current to enter the postsynaptic cell. This current results in a voltage in the extracellular space (the field excitatory post-synaptic potential or field "EPSP") which is recorded by a high impedance recording electrode positioned in the middle of the stratum radiatum of CA1.

For the experiments summarized Table 1, the intensity of the stimulation current was adjusted to produce half-maximal EPSPs (typically about 1.5–2.0 mV). Paired stimulation pulses were given every 40 sec with an interpulse interval of 200 msec (see below). The field EPSPs of the second response were digitized and analyzed to determine amplitude, half-width, and response area. If the responses were stable for 15–30 minutes (baseline), test compounds were added to the perfusion lines for a period of about 15 minutes. The perfusion was then changed back to regular ACSF.

Paired-pulse stimulation was used since stimulation of the SC fibers, in part, activates interneurons which generate an inhibitory postsynaptic potential (IPSP) in the pyramidal cells of CA1. This feed forward IPSP typically sets in after the EPSP reaches its peak. It accelerates the repolarization and shortens the decay phase of the EPSP, and thus could partially mask the effects of the test compounds. One of the relevant features of the feed-forward IPSP is that it can not be reactivated for several hundred milliseconds following a stimulation pulse. This phenomenon can be employed to advantage to eliminate IPSP by delivering paired pulses separated by 200 milliseconds and using the second ("primed") response for data analysis.

The field EPSP recorded in field CA1 after stimulation of CA3 axons is known to be mediated by AMPA receptors: the receptors are present in the synapses [Kessler et al., *Brain Res.* 560: 337–341 (1991)] and drugs that selectively block the receptor selectively block the field EPSP [Muller et al., *Science*, supra]. Aniracetam increases the mean open time of the AMPA receptor channel and as expected from this increases the amplitude of the synaptic current and prolongs its duration [Tang et al. *Science*, supra]. These effects are mirrored in the field EPSP, as reported in the literature [see, for example, Staubli et al., *Psychobiology*, supra; Xiao et al., *Hippocampus* supra; Staubli et al., *Hippocampus* 2: 49–58 (1992)]. Similar results have been reported for the previously disclosed stable benzamide derivatives of aniracetam [International Patent Application Publication No. WO 94/02475 (PCT/US93/06916) (Lynch and Rogers, Regents of the University of California)].

Invention compounds were assayed in the physiological test system described above for the generation of data presented in Table 1 below. In addition, a compound that lacks the rigidity of the benzoxazines of the present invention is also listed as the fifth entry. This serves as a comparison that illustrates the significant increase in activity derived by eliminating the two degrees of rotational freedom inherent in the nonrigid benzyl pyrrolidinone (compare 20% increase in response at 300 µM of compound 1 to 20% at 2 mM for the benzyl pyrrolidinone).

It is also important to recognize that the imide structure of compound 4, which could be considered a rigid model of aniracetam, is inactive in the slice model at 300 µM. Considering the biological activity that has been demonstrated for benzamides wherein the single carbonyl moiety is adjacent to the aromatic ring (Rogers et al., U.S. Pat. No. 5,650,409), one would expect little, or no activity from the acylbenzoxazines of the present invention. It is now apparent however, that whereas the presence of two carbonyl groups in the rigid benzoxazine structure (to provide the imide) is not favorable for biological activity, a single carbonyl moiety in either position is sufficient. Moreover, it is unexpected that the carbonyl in the position alpha to the nitrogen and gamma to the aromatic ring (in contrast to the compounds disclosed in U.S. Pat. No. 5,650,409) produced significantly greater bioavailability and enhanced activity.

The first two data columns of Table 1 show the half-life for plasma clearance (58 min) and the bioavailability (100%) in the rat for the compound of Example 1. These data can be compared with those of the corresponding benzamide (Example 1 of U.S. Pat. No. 5,736,543, issued Apr. 7, 1998), which exhibits a half-life and bioavailability of 31 min and 35%, respectively. The third data column reports the magnitude of the increase in the amplitude of the EPSP at the lowest concentrations that produced a significant increase. The characteristic of a compound to produce an increase in the EPSP response has been a reliable predictor of the ability to improve memory in the 8-arm radial maze task. The last column of Table 1 describes the threshold dose for the most potent compound for enhancing memory in rats that were tested in a learning paradigm using an 8-arm radial maze as described in Staubli et al., *PNAS* 91:11158–1162 (1994).

TABLE 1

| Compound | m | n | R | Half-life* (min) | Bioavailability# (%) | EPSP Response† (conc.) | Maze MED‡ (mg/kg) |
|----------|---|---|------|-----|-----|-------------|-----|
| 1 | 1 | 1 | CH$_2$ | 58 | 100 | 25(300 μM) | NT$^\infty$ |
| 2 | 2 | 1 | CH$_2$ | NT | NT | 20(30 μM) | 0.1 |
| 3 | 2 | 2 | CH$_2$ | NT | NT | 10(30 μM) | NT |
| 4 | 1 | 1 | C=O | NT | NT | 0(300 μM) | NT |
|   |   |   |      | NT | NT | 20 (2 mM) | NT |

*Plasma clearance following iv administration in rat
AUC for oral administration as a percentage of AUC for iv administration
†Percentage increase in the area of the EPSP response
‡Minimum Effective Dose to improve performance of rats in the eight-arm radial maze.
$^\infty$NT = not tested The invention has been described in detail with reference to particular embodiments thereof. It will be understood, however, that variations and modifications can be effected within the spirit and scope of the invention as defined by the following claims.

We claim:

1. A compound having the structure:

wherein:

$X^1$ and $X^2$ are independently selected from H, —NR$^2_2$, —OR$^3$, and —CH$_2$OR$^3$; or $X^1$ and $X^2$ taken together are —OCR$^4_2$O—, —OC$_2$R$^4_4$O—, —OC$_2$R$^4_2$O—, —N=CR$^5$CR$^5$=N—, —OCR$^6$=N—, =N—O—N= or =N—S—N= with the proviso that when $X^1$ and $X^2$ taken together are =N—O—N= or =N—S—N= the compound may be represented by the chemical structure;

each occurrence of R in the (CR$_2$) moiety is independently H, halogen, cyano, hydroxy, C$_1$–C$_6$ alkoxy, C$_1$–C$_3$ fluoroalkoxy, thiol, C$_1$–C$_6$ alkyl, C$_1$–C$_3$ fluoroalkyl, C$_2$–C$_6$ alkoxyalkyl, C$_6$–C$_{12}$ aryl, C$_3$–C$_{12}$ heteroaryl, C$_7$–C$_{12}$ arylalkyl, C$_4$–C$_{12}$ heteroarylalkyl, C$_6$–C$_{12}$ aryloxy, C$_7$–C$_{12}$ aryloxyalkyl, C$_7$–C$_{12}$ arylalkoxy, C$_4$–C$_{12}$ heteroarylalkoxy, carboxyalkyl, or both R groups together are =O;

each occurrence of R$^1$ is independently H, C$_1$–C$_6$ alkyl, C$_1$–C$_3$ fluoroalkyl, aryl, heteroaryl, arylalkyl, or heteroarylalkyl;

each occurrence of R$^2$ is independently H, C$_1$–C$_6$ alkyl, C$_1$–C$_3$ fluoroalkyl, C$_6$–C$_{12}$ aryl, C$_3$–C$_{12}$ heteroaryl, C$_7$–C$_{12}$ arylalkyl, C$_4$–C$_{12}$ heteroarylalkyl, or both R$^2$ groups together form a carbocyclic ring that includes the nitrogen atom;

each occurrence of R$^3$ is independently H, C$_1$–C$_6$ alkyl, C$_1$–C$_3$ fluoroalkyl, C$_2$–C$_6$ alkoxyalkyl, C$_7$–C$_{12}$ aryloxyalkyl, C$_7$–C$_{12}$ arylalkyl, or C$_4$–C$_{12}$ heteroarylalkyl;

each occurrence of R$^4$ is independently H, halogen, cyano, carboxyalkyl, carboxamido, C$_1$–C$_6$ alkyl, C$_1$–C$_3$ fluoroalkyl, C$_2$–C$_6$ alkoxyalkyl, C$_7$–C$_{12}$ aryloxyalkyl, C$_7$–C$_{12}$ arylalkyl, or C$_4$–C$_{12}$ heteroarylalkyl;

each occurrence of R$^5$ is independently H, cyano, hydroxy, C$_1$–C$_6$ alkoxy, C$_1$–C$_6$ alkyl, C$_1$–C$_3$ fluoroalkyl, C$_2$–C$_6$ alkoxyalkyl, or C$_7$–C$_{12}$ arylalkyl, C$_4$–C$_{12}$ heteroarylalkyl, C$_6$–C$_{12}$ aryloxy, C$_7$–C$_{12}$ aryloxyalkyl, C$_7$–C$_{12}$ arylalkoxy, or C$_4$–C$_{12}$ heteroarylalkoxy;

each occurrence of R$^6$ is independently H, C$_1$–C$_6$ alkyl, C$_1$–C$_3$ fluoroalkyl, C$_7$–C$_{12}$ arylalkyl or C$_4$–C$_{12}$ heteroarylalkyl;

Z is O or S and n is 1, 2, 3, or 4.

2. A compound in accordance with claim 1 in which both $X^1$ and $X^2$ taken together are —OCR$^4_2$O—, —OC$_2$R$^4_4$O—, or —OC$_2$R$^4_2$O—; and n is 2 or 3.

3. A compound in accordance with claim 1 in which both $X^1$ and $X^2$ taken together are —N=CR$^5_2$CR$^5_2$=N—; and n is 2 or 3.

4. A compound in accordance with claim 1 in which both $X^1$ and $X^2$ taken together are —OCR$^6$=N—; and n is 2 or 3.

5. A compound in accordance with claim 1 in which both $X^1$ and $X^2$ taken together are =N—O—N= or =N—S—N=; and n is 2 or 3.

6. A compound in accordance with claim 5 in which both $X^1$ and $X^2$ taken together are =N—O—N=.

7. A compound in accordance with claim 2 wherein each occurrence of R in the (CR$_2$) moiety is independently H, fluoro, cyano, hydroxy, $C_1$–$C_6$ alkoxy, $C_1$–$C_3$ fluoroalkoxy, $C_1$–$C_6$ alkyl, $C_1$–$C_3$ fluoroalkyl, $C_2$–$C_6$ alkoxyalkyl, $C_3$–$C_{12}$ heteroaryl, $C_7$–$C_{12}$ arylalkyl, $C_4$–$C_{12}$ heteroarylalkyl, $C_6$–$C_{12}$ aryloxy, $C_7$–$C_{12}$ aryloxyalkyl, $C_7$–$C_{12}$ arylalkoxy, $C_4$–$C_{12}$ heteroarylalkoxy, or both R groups together are =O; and each occurrence of $R^1$ is independently H, arylalkyl, or heteroarylalkyl; and each occurrence of $R^4$ is independently H, fluoro, cyano, carboxyalkyl, $C_1$–$C_6$ alkyl, $C_1$–$C_3$ fluoroalkyl, $C_2$–$C_6$ alkoxyalkyl, $C_7$–$C_{12}$ aryloxyalkyl, $C_7$–$C_{12}$ arylalkyl, or $C_4$–$C_{12}$ heteroarylalkyl.

8. A compound in accordance with claim 3 in which each occurrence of R is independently H, fluoro, cyano, hydroxy, $C_1$–$C_6$ alkoxy, $C_1$–$C_3$ fluoroalkoxy, $C_1$–$C_6$ alkyl, $C_1$–$C_3$ fluoroalkyl, $C_2$–$C_6$ alkoxyalkyl, $C_3$–$C_{12}$ heteroaryl, $C_7$–$C_{12}$ arylalkyl, $C_4$–$C_{12}$ heteroarylalkyl, $C_6$–$C_{12}$ aryloxy, $C_7$–$C_{12}$ aryloxyalkyl, $C_7$–$C_{12}$ arylalkoxy, $C_4$–$C_{12}$ heteroarylalkoxy, or both R groups together are =O; and each occurrence of $R^1$ is independently H, arylalkyl, or heteroarylalkyl.

9. A compound in accordance with claim 4 in which each occurrence of R is independently H, fluoro, cyano, hydroxy, $C_1$–$C_6$ alkoxy, $C_1$–$C_3$ fluoroalkoxy, $C_1$–$C_6$ alkyl, $C_1$–$C_3$ fluoroalkyl, $C_2$–$C_6$ alkoxyalkyl, $C_3$–$C_{12}$ heteroaryl, $C_7$–$C_{12}$ arylalkyl, $C_4$–$C_{12}$ heteroarylalkyl, $C_6$–$C_{12}$ aryloxy, $C_7$–$C_{12}$ aryloxyalkyl, $C_7$–$C_{12}$ arylalkoxy, $C_4$–$C_{12}$ heteroarylalkoxy, or both R groups together are =O; and each occurrence of $R^1$ is independently H, arylalkyl, or heteroarylalkyl.

10. A compound in accordance with claim 6 in which each occurrence of R is independently H, fluoro, cyano, hydroxy, $C_1$–$C_6$ alkoxy, $C_1$–$C_3$ fluoroalkoxy, $C_1$–$C_6$ alkyl, $C_1$–$C_3$ fluoroalkyl, $C_2$–$C_6$ alkoxyalkyl, $C_3$–$C_{12}$ heteroaryl, $C_7$–$C_{12}$ arylalkyl, $C_4$–$C_{12}$ heteroarylalkyl, $C_6$–$C_{12}$ aryloxy, $C_7$–$C_{12}$ aryloxyalkyl, $C_7$–$C_{12}$ arylalkoxy, $C_4$–$C_{12}$ heteroarylalkoxy, or both R groups together are =O; and each occurrence of $R^1$ is independently H, arylalkyl, or heteroarylalkyl.

11. The compound in accordance with claim 1 which is 5a,6,7,8-tetrahydro-1,3-dioxolo[4,5-g]pyrrolo[2,1-b][1,3]benzoxazine-8(10H)-one.

12. A compound in accordance with claim 1 which is 6a,7,8,9-tetrahydro-1,4-dioxin[2,3-g]pyrrolo[2,1-b][1,3]benzoxazine-9(11H)-one.

13. A compound in accordance with claim 1 which is 6a,7,8,9-tetrahydro-1,4-dioxan[2,3-g]pyrido[2,1-b][1,3]benzoxazine-10(10H,12H)-dione.

14. A method for improving the performance of a subject on sensory-motor problems or cognitive tasks dependent upon brain networks utilizing AMPA receptors, wherein the strength of memory encoding by said subject is improved, or wherein brain functioning is improved in subjects having deficiencies in the number of excitatory synapses or AMPA receptors, said method comprising administering to said subject an effective amount of a compound having the formula:

wherein:

$X^1$ and $X^2$ are independently selected from the H, —NR$^2_2$, —OR$^3$, and —CH$_2$OR$^3$; or $X^1$ and $X^2$ taken together are —OCR$^4_2$O—, —OC$_2$R$^4_4$O—, —OC$_2$R$^4_2$O—, —N=CR$^5$CR$^5$=N—, —OCR$^6$=N—, =N—O—N= or =N—S—N= with the proviso that when $X^1$ and $X^2$ taken together are =N—O—N= or =N—S—N= the compound may be represented by the chemical structure:

each occurrence of R is independently H, halogen, cyano, hydroxy, $C_1$–$C_6$ alkoxy, $C_1$–$C_3$ fluoroalkoxy, thiol, $C_1$–$C_6$ alkyl, $C_1$–$C_3$ fluoroalkyl, $C_2$–$C_6$ alkoxyalkyl, $C_6$–$C_{12}$ aryl, $C_3$–$C_{12}$ heteroaryl, $C_7$–$C_{12}$ arylalkyl, $C_4$–$C_{12}$ heteroarylalkyl, $C_6$–$C_{12}$ aryloxy, $C_7$–$C_{12}$ aryloxyalkyl, $C_1$–$C_{12}$ arylalkoxy, $C_4$–$C_{12}$ heteroarylalkoxy, carboxyalkyl, or both R groups together are =O;

each occurrence of $R^1$ is independently H, $C_1$–$C_6$ alkyl, $C_1$–$C_3$ fluoroalkyl, aryl, heteroaryl, arylalkyl, or heteroarylalkyl;

each occurrence of $R^2$ is independently H, $C_1$–$C_6$ alkyl, $C_1$–$C_3$ fluoroalkyl, $C_6$–$C_{12}$ aryl, $C_3$–$C_{12}$ heteroaryl, $C_7$–$C_{12}$ arylalkyl, $C_4$–$C_{12}$ heteroarylalkyl, or both $R^2$ groups together form a carbocyclic ring that includes the nitrogen atom;

each occurrence of $R^3$ is independently H, $C_1$–$C_6$ alkyl, $C_1$–$C_3$ fluoroalkyl, $C_2$–$C_6$ alkoxyalkyl, $C_7$–$C_{12}$ aryloxyalkyl, $C_7$–$C_{12}$ arylalkyl, or $C_4$–$C_{12}$ heteroarylalkyl;

each occurrence of $R^4$ is independently H, halogen, cyano, carboxyalkyl, carboxamido, $C_1$–$C_6$ alkyl, $C_1$–$C_3$ fluoroalkyl, $C_2$–$C_6$ alkoxyalkyl, $C_7$–$C_{12}$ aryloxyalkyl, $C_7$–$C_{12}$ arylalkyl, or $C_4$–$C_{12}$ heteroarylalkyl;

each occurrence of $R^5$ is independently H, cyano, hydroxy, $C_1$–$C_6$ alkoxy, $C_1$–$C_6$ alkyl, $C_1$–$C_3$ fluoroalkyl, $C_2$–$C_6$ alkoxyalkyl, or $C_7$–$C_{12}$ arylalkyl, $C_4$–$C_{12}$ heteroarylalkyl, $C_6$–$C_{12}$ aryloxy, $C_7$–$C_{12}$ aryloxyalkyl, $C_7$–$C_{12}$ arylalkoxy, or $C_4$–$C_{12}$ heteroarylalkoxy;

each occurrence of $R^6$ is independently H, $C_1$–$C_6$ alkyl, $C_1$–$C_3$ fluoroalkyl, $C_7$–$C_{12}$ arylalkyl or $C_4$–$C_{12}$ heteroarylalkyl;

Z is O or S and n is 1, 2, 3, or 4.

15. A method for decreasing the amount of time needed for a subject to learn a cognitive, motor or perceptual task, or for increasing the time for which said subject retains cognitive, motor or perceptual tasks, or for decreasing the quantity or severity of errors made by a subject in recalling a cognitive, motor or perceptual task, said method comprising administering to said subject an effective amount of a compound having the formula:

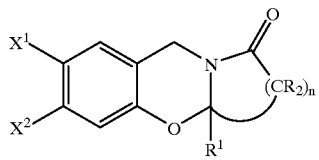

wherein:

X$^1$ and X$^2$ are independently selected from the H, —NR$^2{}_2$, —OR$^3$, and —CH$_2$OR$^3$; or X$^1$ and X$^2$ taken together are —OCR$^4{}_2$O—, —OC$_2$R$^4{}_4$O—, —OC$_2$R$^4{}_2$O—, —N=CR$^5$CR$^5$=N—, —OCR$^6$=N—, =N—O—N= or =N—S—N= with the proviso that when X$^1$ and X$^2$ taken together are =N—O—N= or =N—S—N= the compound may be represented by the chemical structure;

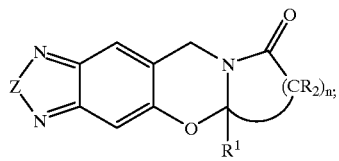

each occurrence of R is independently H, halogen, cyano, hydroxy, C$_1$–C$_6$ alkoxy, C$_1$–C$_3$ fluoroalkoxy, thiol, C$_1$–C$_6$ alkyl, C$_1$–C$_3$ fluoroalkyl, C$_2$–C$_6$ alkoxyalkyl, C$_6$–C$_{12}$ aryl, C$_3$–C$_{12}$ heteroaryl, C$_7$–C$_{12}$ arylalkyl, C$_4$–C$_{12}$ heteroarylalkyl, C$_6$–C$_{12}$ aryloxy, C$_7$–C$_{12}$ aryloxyalkyl, C$_7$–C$_{12}$ arylalkoxy, C$_4$–C$_{12}$ heteroarylalkoxy, carboxyalkyl, or both R groups together are =O;

each occurrence of R$^1$ is independently H, C$_1$–C$_6$ alkyl, C$_1$–C$_3$ fluoroalkyl, aryl, heteroaryl, arylalkyl, or heteroarylalkyl;

each occurrence of R$^2$ is independently H, C$_1$–C$_6$ alkyl, C$_1$–C$_3$ fluoroalkyl, C$_6$–C$_{12}$ aryl, C$_3$–C$_{12}$ heteroaryl, C$_7$–C$_{12}$ arylalkyl, C$_4$–C$_{12}$ heteroarylalkyl, or both R$^2$ groups together form a carbocyclic ring that includes the nitrogen atom;

each occurrence of R$^3$ is independently H, C$_1$–C$_6$ alkyl, C$_1$–C$_3$ fluoroalkyl, C$_2$–C$_6$ alkoxyalkyl, C$_7$–C$_{12}$ aryloxyalkyl, C$_7$–C$_{12}$ arylalkyl, or C$_4$–C$_{12}$ heteroarylalkyl;

each occurrence of R$^4$ is independently H, halogen, cyano, carboxyalkyl, carboxamido, C$_1$–C$_6$ alkyl, C$_1$–C$_3$ fluoroalkyl, C$_2$–C$_6$ alkoxyalkyl, C$_7$–C$_{12}$ aryloxyalkyl, C$_7$–C$_{12}$ arylalkyl, or C$_4$–C$_{12}$ heteroarylalkyl;

each occurrence of R$^5$ is independently H, cyano, hydroxy, C$_1$–C$_6$ alkoxy, C$_1$–C$_6$ alkyl, C$_1$–C$_3$ fluoroalkyl, C$_2$–C$_6$ alkoxyalkyl, or C$_7$–C$_{12}$ arylalkyl, C$_4$–C$_{12}$ heteroarylalkyl, C$_6$–C$_{12}$ aryloxy, C$_7$–C$_{12}$ aryloxyalkyl, C$_7$–C$_{12}$ arylalkoxy, or C$_4$–C$_{12}$ heteroarylalkoxy;

each occurrence of R$^6$ is independently H, C$_1$–C$_6$ alkyl, C$_1$–C$_3$ fluoroalkyl, C$_7$–C$_{12}$ arylalkyl or C$_4$–C$_{12}$ heteroarylalkyl;

Z is O or S and n is 1, 2, 3, or 4.

16. A method for the treatment of a human subject to enhance synaptic response mediated by AMPA receptors, said method comprising administering to said subject an effective amount of a compound having the formula:

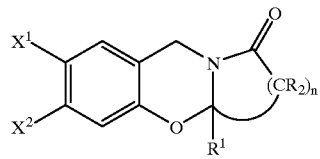

wherein:

X$^1$ and X$^2$ are independently selected from the H, —NR$^2{}_2$, —OR$^3$, and —CH$_2$OR$^3$; or X$^1$ and X$^2$ taken together are —OCR$^4{}_2$O—, —OC$_2$R$^4{}_4$O—, —OC$_2$R$^4{}_2$O—, —N=CR$^5$CR$^5$=N—, —OCR$^6$=N—, =N—O—N= or =N—S—N= with the proviso that when X$^1$ and X$^2$ taken together are =N—O—N= or =N—S—N= the compound may be represented by the chemical structure:

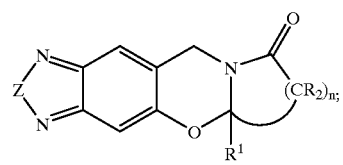

each occurrence of R is independently H, halogen, cyano, hydroxy, C$_1$–C$_6$ alkoxy, C$_1$–C$_3$ fluoroalkoxy, thiol, C$_1$–C$_6$ alkyl, C$_1$–C$_3$ fluoroalkyl, C$_2$–C$_6$ alkoxyalkyl, C$_6$–C$_{12}$ aryl, C$_3$–C$_{12}$ heteroaryl, C$_7$–C$_{12}$ arylalkyl, C$_4$C$_{12}$ heteroarylalkyl, C$_6$–C$_{12}$ aryloxy, C$_7$–C$_{12}$ aryloxyalkyl, C$_7$–C$_{12}$ arylalkoxy, C$_4$–C$_{12}$ heteroarylalkoxy, carboxyalkyl, or both R groups together are =O;

each occurrence of R$^1$ is independently H, C$_1$–C$_6$ alkyl, C$_1$–C$_3$ fluoroalkyl, aryl, heteroaryl, arylalkyl, or heteroarylalkyl;

each occurrence of R$^2$ is independently H, C$_1$–C$_6$ alkyl, C$_1$–C$_3$ fluoroalkyl, C$_6$–C$_{12}$ aryl, C$_3$–C$_{12}$ heteroaryl, C$_7$–C$_{12}$ arylalkyl, C$_4$–C$_{12}$ heteroarylalkyl, or both R$^2$ groups together form a carbocyclic ring that includes the nitrogen atom;

each occurrence of R$^3$ is independently H, C$_1$–C$_6$ alkyl, C$_1$–C$_3$ fluoroalkyl, C$_2$–C$_6$ alkoxyalkyl, C$_7$–C$_{12}$ aryloxyalkyl, C$_7$–C$_{12}$ arylalkyl, or C$_4$–C$_{12}$ heteroarylalkyl;

each occurrence of R$^4$ is independently H, halogen, cyano, carboxyalkyl, carboxamido, C$_1$–C$_6$ alkyl, C$_1$–C$_3$ fluoroalkyl, C$_2$–C$_6$ alkoxyalkyl, C$_7$–C$_{12}$ aryloxyalkyl, C$_7$–C$_{12}$ arylalkyl, or C$_4$–C$_{12}$ heteroarylalkyl;

each occurrence of R$^5$ is independently H, cyano, hydroxy, C$_1$–C$_6$ alkoxy, C$_1$–C$_6$ alkyl, C$_1$–C$_3$ fluoroalkyl, C$_2$–C$_6$ alkoxyalkyl, or C$_7$–C$_{12}$ arylalkyl, C$_4$–C$_{12}$ heteroarylalkyl, C$_6$–C$_{12}$ aryloxy, C$_7$–C$_{12}$ aryloxyalkyl, C$_7$–C$_{12}$ arylalkoxy, or C$_4$–C$_{12}$ heteroarylalkoxy;

each occurrence of R$^6$ is independently H, C$_1$–C$_6$ alkyl, C$_1$–C$_3$ fluoroalkyl, C$_7$–C$_{12}$ arylalkyl or C$_4$–C$_{12}$ heteroarylalkyl;

Z is O or S and n is 1, 2, 3, or 4.

17. A method for the treatment of schizophrenia, schizophreniform behavior, or depression in a human subject, said method comprising administering to a human subject in need of such treatment a compound in a therapeutically effective amount, said compound having the structure:

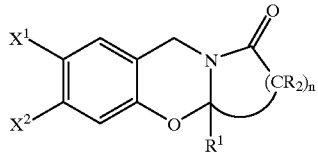

wherein:

$X^1$ and $X^2$ are independently selected from the H, $-NR^2_2$, $-OR^3$, and $-CH_2OR^3$; or $X^1$ and $X^2$ taken together are $-OCR^4_2O-$, $-OC_2R^4_4O-$, $-OC_2R^4_2O-$, $-N=CR^5CR^5=N-$, $-OCR^6=N-$, $=N-O-N=$ or $=N-S-N=$ with the proviso that when $X^1$ and $X^2$ taken together are $=N-O-N=$ or $=N-S-N=$ the compound may be represented by the chemical structure:

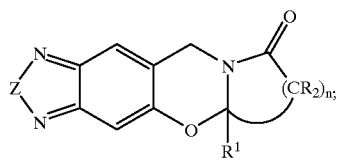

each occurrence of R is independently H, halogen, cyano, hydroxy, $C_1-C_6$ alkoxy, $C_1-C_3$ fluoroalkoxy, thiol, $C_1-C_6$ alkyl, $C_1-C_3$ fluoroalkyl, $C_2-C_6$ alkoxyalkyl, $C_6-C_{12}$ aryl, $C_3-C_{12}$ heteroaryl, $C_7-C_{12}$ arylalkyl, $C_4-C_{12}$ heteroarylalkyl, $C_6-C_{12}$ aryloxy, $C_7-C_{12}$ aryloxyalkyl, $C_7-C_{12}$ arylalkoxy, $C_4-C_{12}$ heteroarylalkoxy, carboxyalkyl, or both R groups together are $=O$;

each occurrence of $R^1$ is independently H, $C_1-C_6$ alkyl, $C_1-C_3$ fluoroalkyl, aryl, heteroaryl, arylalkyl, or heteroarylalkyl;

each occurrence of $R^2$ is independently H, $C_1-C_6$ alkyl, $C_1-C_3$ fluoroalkyl, $C_6C_{12}$ aryl, $C_3-C_{12}$ heteroaryl, $C_7-C_{12}$ arylalkyl, $C_4-C_{12}$ heteroarylalkyl, or both $R^2$ groups together form a carbocyclic ring that includes the nitrogen atom;

each occurrence of $R^3$ is independently H, $C_1-C_6$ alkyl, $C_1-C_3$ fluoroalkyl, $C_2-C_6$ alkoxyalkyl, $C_7-C_{12}$ aryloxyalkyl, $C_7-C_{12}$ arylalkyl, or $C_4-C_{12}$ heteroarylalkyl;

each occurrence of $R^4$ is independently H, halogen, cyano, carboxyalkyl, carboxamido, $C_1-C_6$ alkyl, $C_1-C_3$ fluoroalkyl, $C_2-C_6$ alkoxyalkyl, $C_7-C_{12}$ aryloxyalkyl, $C_7-C_{12}$ arylalkyl, or $C_4-C_{12}$ heteroarylalkyl;

each occurrence of $R^5$ is independently H, cyano, hydroxy, $C_1-C_6$ alkoxy, $C_1-C_6$ alkyl, $C_1-C_3$ fluoroalkyl, $C_2-C_6$ alkoxyalkyl, or $C_7-C_{12}$ arylalkyl, $C_4-C_{12}$ heteroarylalkyl, $C_6-C_{12}$ aryloxy, $C_7-C_{12}$ aryloxyalkyl, $C_7-C_{12}$ arylalkoxy, or $C_4-C_{12}$ heteroarylalkoxy;

each occurrence of $R^6$ is independently H, $C_1-C_6$ alkyl, $C_1-C_3$ fluoroalkyl, $C_7-C_{12}$ arylalkyl or $C_4-C_{12}$ heteroarylalkyl;

Z is O or S and n is 1, 2, 3, or 4.

18. A pharmaceutical composition comprising an effective amount of at least one compound according to claim 1.

19. A pharmaceutical composition comprising an effective amount of at least one compound according to claim 2.

20. A pharmaceutical composition comprising an effective amount of at least one compound according to claim 3.

21. A pharmaceutical composition comprising an effective amount of at least one compound according to claim 4.

22. A pharmaceutical composition comprising an effective amount of at least one compound according to claim 5.

23. A pharmaceutical composition comprising an effective amount of at least one compound according to claim 6.

* * * * *